(12) United States Patent
Hussain et al.

(10) Patent No.: US 10,957,043 B2
(45) Date of Patent: Mar. 23, 2021

(54) AI SYSTEMS FOR DETECTING AND SIZING LESIONS

(71) Applicant: EndoSoft LLC, Schenectady, NY (US)

(72) Inventors: Zohair Hussain, Schenectady, NY (US); Rakesh Madan, Schenectady, NY (US)

(73) Assignee: ENDOSOFT LLC, Schenectady, NY (US)

( * ) Notice: Subject to any disclaimer, the term of this patent is extended or adjusted under 35 U.S.C. 154(b) by 150 days.

(21) Appl. No.: 16/288,843

(22) Filed: Feb. 28, 2019

(65) Prior Publication Data

US 2020/0279373 A1 Sep. 3, 2020

(51) Int. Cl.
*G06T 7/00* (2017.01)
*G06T 7/62* (2017.01)
(Continued)

(52) U.S. Cl.
CPC .......... *G06T 7/0014* (2013.01); *A61B 5/4255* (2013.01); *A61B 5/7267* (2013.01); *A61B 90/37* (2016.02); *G06T 7/13* (2017.01); *G06T 7/62* (2017.01); *A61B 2090/373* (2016.02); *G06T 2207/10016* (2013.01); *G06T 2207/10068* (2013.01); *G06T 2207/20081* (2013.01);
(Continued)

(58) Field of Classification Search
CPC .......... G06T 7/0014; G06T 7/62; G06T 7/13; G06T 2207/10016; G06T 2207/10068; G06T 2207/20081; G06T 2207/20084; G06T 2207/30032; G06T 2207/30096; A61B 90/37; A61B 5/4255; A61B 5/7267; A61B 2090/373
See application file for complete search history.

(56) References Cited

U.S. PATENT DOCUMENTS

| | | | | |
|---|---|---|---|---|
| 5,984,870 A | * | 11/1999 | Giger | G06T 7/0012 600/443 |
| 6,351,573 B1 | * | 2/2002 | Schneider | G16H 20/40 382/294 |

(Continued)

FOREIGN PATENT DOCUMENTS

WO 2018180631 A1 4/2018

OTHER PUBLICATIONS

Zhang et al., 2017, IEEE, "Automatic Detection and Classification of Colorectal Polyps by Transferring Low-Level CNN Features From Nonmedical Domain" (pp. 41-47). (Year: 2017).*

(Continued)

*Primary Examiner* — Manav Seth
(74) *Attorney, Agent, or Firm* — Hoffman Warnick LLC

(57) ABSTRACT

An artificial intelligence (AI) platform, method and program product for detecting and sizing a lesion in real time during a clinical procedure. An AI platform is disclosed that includes: a trained classifier that includes a deep learning model trained to detect lesions and reference objects in image data; a real time video analysis system that receives a video feed during a clinical procedure, uses the trained classifier to determine if a video frame from the video feed has both a lesion and a reference object, calculates an actual size of the lesion based on a pixel size of both the lesion and the reference object, and outputs an indication that the lesion was detected and the actual size of the lesion.

19 Claims, 11 Drawing Sheets

(51) Int. Cl.
*G06T 7/13* (2017.01)
*A61B 5/00* (2006.01)
*A61B 90/00* (2016.01)

(52) U.S. Cl.
CPC .............. *G06T 2207/20084* (2013.01); *G06T 2207/30032* (2013.01); *G06T 2207/30096* (2013.01)

(56) References Cited

U.S. PATENT DOCUMENTS

| | | | |
|---|---|---|---|
| 6,757,415 B1 * | 6/2004 | Rogers | G06K 9/4609 382/130 |
| 7,474,775 B2 * | 1/2009 | Abramoff | G06K 9/6277 351/206 |
| 7,499,578 B2 * | 3/2009 | Reeves | G06T 3/0075 382/128 |
| 7,646,902 B2 * | 1/2010 | Chan | G06K 9/00 382/128 |
| 8,144,963 B2 * | 3/2012 | Cascio | G06T 7/0012 382/131 |
| 8,543,519 B2 * | 9/2013 | Guyon | G06T 7/62 706/12 |
| 8,634,607 B2 * | 1/2014 | Levenson | G01J 3/453 382/128 |
| 8,900,113 B2 * | 12/2014 | Raleigh | A61N 5/1037 600/1 |
| 9,014,447 B2 * | 4/2015 | Slabaugh | G06T 7/0012 382/131 |
| 9,117,133 B2 * | 8/2015 | Barnes | A61B 5/7246 |
| 9,125,570 B2 * | 9/2015 | Pelc | A61B 6/4028 |
| 9,208,556 B2 * | 12/2015 | Giger | G06K 9/6253 |
| 9,445,713 B2 * | 9/2016 | Douglas | A61B 1/00045 |
| 9,589,374 B1 | 3/2017 | Gao et al. | |
| 9,700,213 B2 | 7/2017 | Tajbakhsh et al. | |
| 9,741,116 B2 | 8/2017 | Liang et al. | |
| 9,747,687 B2 | 8/2017 | Tajbakhsh et al. | |
| 9,760,983 B2 * | 9/2017 | Yan | G06T 7/30 |
| 9,830,699 B2 * | 11/2017 | Cales | G06T 7/11 |
| 9,990,472 B2 * | 6/2018 | Gurcan | G16H 30/20 |
| 10,055,843 B2 | 8/2018 | Tajbakhsh et al. | |
| 10,121,243 B2 * | 11/2018 | Boroczky | G06F 19/00 |
| 10,127,433 B2 * | 11/2018 | Ascierto | G06K 9/00127 |
| 10,192,099 B2 * | 1/2019 | Agaian | G06T 7/181 |
| 10,269,118 B2 * | 4/2019 | Cales | G06T 7/11 |
| 10,510,144 B2 * | 12/2019 | Zur | G06T 7/0012 |
| 10,559,080 B2 * | 2/2020 | Hazan | G06T 7/0012 |
| 2005/0078858 A1 * | 4/2005 | Yao | G06T 7/149 382/128 |
| 2009/0118600 A1 * | 5/2009 | Ortiz | A61B 5/0064 600/306 |
| 2010/0111387 A1 * | 5/2010 | Christiansen, II | A61B 5/445 382/128 |
| 2013/0041219 A1 | 2/2013 | Hasegawa et al. | |
| 2015/0080652 A1 | 3/2015 | Staples, II et al. | |
| 2015/0150457 A1 * | 6/2015 | Wu | A61B 5/445 600/425 |
| 2015/0216953 A1 * | 8/2015 | First | C12Y 304/24069 424/62 |
| 2015/0374210 A1 | 12/2015 | Durr et al. | |
| 2016/0100789 A1 * | 4/2016 | Huang | A61B 5/7246 600/306 |
| 2017/0164924 A1 * | 6/2017 | Urabe | G06T 7/62 |
| 2018/0014777 A1 * | 1/2018 | Amir | G16H 40/20 |
| 2018/0075599 A1 * | 3/2018 | Tajbakhsh | G06T 1/0007 |
| 2018/0096191 A1 | 4/2018 | Wan et al. | |
| 2018/0103892 A1 * | 4/2018 | Kaur | G06T 7/136 |
| 2018/0253839 A1 * | 9/2018 | Zur | G06T 7/0012 |
| 2018/0256025 A1 * | 9/2018 | Yi | A61B 5/14532 |
| 2018/0263568 A1 | 9/2018 | Yi et al. | |
| 2018/0279943 A1 * | 10/2018 | Budman | G06F 19/321 |
| 2019/0220738 A1 * | 7/2019 | Flank | G16H 50/20 |
| 2019/0347790 A1 * | 11/2019 | Lee | G06T 7/0012 |
| 2020/0160980 A1 * | 5/2020 | Lyman | G06T 11/001 |

OTHER PUBLICATIONS

Kim et al., Mar. 2016, World Journal of Gastroenterology, Is forceps more useful than visualization for measurement of colon polyp size? (pp. 3220-3226). (Year: 2016).*

Byrne MF, et al.; "Real-time differentiation of adenomatous and hyperplastic diminutive colorectal polyps during analysis of unaltered videos of standard colonoscopy using a deep learning model"; GUT 2019;68; pp. 94-100.

International Search Report and Written Opinion dated Sep. 4, 2019 for PCT/US2019/038431 filed Jun. 21, 2019; pp. 14.

* cited by examiner

```xml
<data>
    <image_id>{8D727F3E-3C7A-410B-B69B-70E2562AFAFE}</image_id>
    <item>
        <class_name>forceps</class_name>
        <score>99</score>
        <left>442</left>
        <right>623</right>
        <top>642</top>
        <bottom>982</bottom>
    </item>
    <item>
        <class_name>polyp</class_name>
        <score>99</score>
        <left>165</left>
        <right>513</right>
        <top>540</top>
        <bottom>845</bottom>
    </item>
</data>
```

Figure 4

AI SYSTEMS FOR DETECTING AND SIZING LESIONS

TECHNICAL FIELD

The subject matter of this invention relates to detecting and sizing lesions and more particularly to an artificial intelligence platform for detecting and sizing lesions in real time.

BACKGROUND

Colon polyps are growths on the inner lining of the colon and are very common. Colon polyps are significant because they may be or may become malignant (cancerous). They also are important because based on their size, number, and microscopic anatomy (histology), a clinician can predict which patients are more likely to develop more polyps and colon cancer.

Polyps may take on various shapes. For example, pedunculated polyps look like a mushroom, are attached to the lining of the colon by a thin stalk and flop around inside the intestine. Sessile polyps do not have a stalk and are attached to the lining by a broad base. Flat colon polyps are flat or even slightly depressed. These may be difficult to identify because they are not as prominent as polypoid or sessile polyps with the commonly-available methods of diagnosing polyps.

The most common type of polyp is the adenoma or adenomatous polyp. It is an important type of polyp to identify not only because it is the most common, but because it is the most common risk factor for colon cancer. The likelihood that an adenoma will develop into (or has already developed into) cancer is partially dependent on its type, shape and size; the larger the polyp, the more likely it is that the polyp is or will become malignant (e.g., concern about the potential malignancy increases with a polyp size greater than one centimeter in size).

It also matters if there is a single polyp or multiple polyps. Patients with multiple polyps, even if they are not malignant when examined under the microscope are more likely to develop additional polyps in the future that may become malignant. Concern about this increasing malignancy potential begins when there are three or more polyps.

Since there is a strong link between polyp size and the subsequent development of malignancy, it is essential that polyps are detected and sized accurately. The most common approach for sizing a polyp involves an endoscopist viewing a high definition screen during a procedure and visually estimating its size. Polyps removed during the procedure, e.g., using forceps or a snare, can thereafter be further measured by a pathologist. A recent study by the NIH however found significant discrepancies (e.g., an average difference of 0.3 cm) between the endoscopist's estimation and pathologist's measurement of colonic polyp size.

The results of the study suggest a wide variance in polyp size documentation. Neither clinician estimate nor pathologist measurement accurately reflects colonic polyp size. Inaccurate determination of polyp size can negatively impact patient outcomes involving advanced adenoma detection.

SUMMARY

Aspects of the disclosure provide an artificial intelligence (AI) platform for detecting and sizing lesions (e.g., polyps) and other diseased tissue during procedures in real time. Accordingly, using the described platform and approach, clinicians can for example detect and size flat or sessile serrated polyps in real time while doing a procedure on a patient, thus promoting better patient care. The AI platform uses a two-step process while the clinician is doing the procedure in real time, in which lesions are first detected and then sized using a reference object like forceps or any other device used during the procedure for intervention. A deep learning algorithm predicts the context of a video stream collected during a clinical procedure for interventions, in which the context identifies, e.g., colon polyps (lesions) and forceps (reference objects).

A first aspect discloses an artificial intelligence (AI) platform for detecting and sizing a lesion in real time during a clinical procedure, comprising: a trained classifier that includes a deep learning model trained to detect lesions and reference objects in image data; a real time video analysis system that receives a video feed during a clinical procedure, uses the trained classifier to determine if a video frame from the video feed has both a lesion and a reference object, calculates an actual size of the lesion based on a pixel size of both the lesion and the reference object, and outputs an indication that the lesion was detected and the actual size of the lesion.

A second aspect discloses a method for detecting and sizing a lesion in real time during a clinical procedure using artificial intelligence (AI), comprising: providing a trained classifier that includes a deep learning model trained to detect lesions and reference objects in image data; processing a video feed during a clinical procedure; using the trained classifier to determine if a video frame from the video feed has both a lesion and a reference object; calculating an actual size of the lesion based on a pixel size of both the lesion and the reference object; and outputting an indication that the lesion was detected and the actual size of the lesion.

A third aspect discloses a computer program product stored on a computer readable storage medium, which when executed by a computing system, detects and sizes a lesion in real time during a clinical procedure using artificial intelligence (AI), the program product comprising: program code that processes a video feed during a clinical procedure; program code that uses a trained classifier to determine if a video frame from the video feed has both a lesion and a reference object; program code that calculates an actual size of the lesion based on a pixel size of both the lesion and the reference object; and program code that outputs an indication that the lesion was detected and the actual size of the lesion.

A fourth aspect discloses a method for detecting the lesion in a saved video, e.g., collected from a Video Capsule Endoscopy (VCE) procedure, using artificial intelligence (AI), the method comprising: providing a trained classifier that includes a deep learning model trained to detect lesions; processing a video after it has been created using images transferred from a recorder; and using the trained classifier to determine if a video frame from the video has a lesion.

BRIEF DESCRIPTION OF THE DRAWINGS

These and other features of this invention will be more readily understood from the following detailed description of the various aspects of the invention taken in conjunction with the accompanying drawings in which:

FIG. 4 shows an XML output of an analyzed image using a trained classifier according to embodiments.

Figure 1:
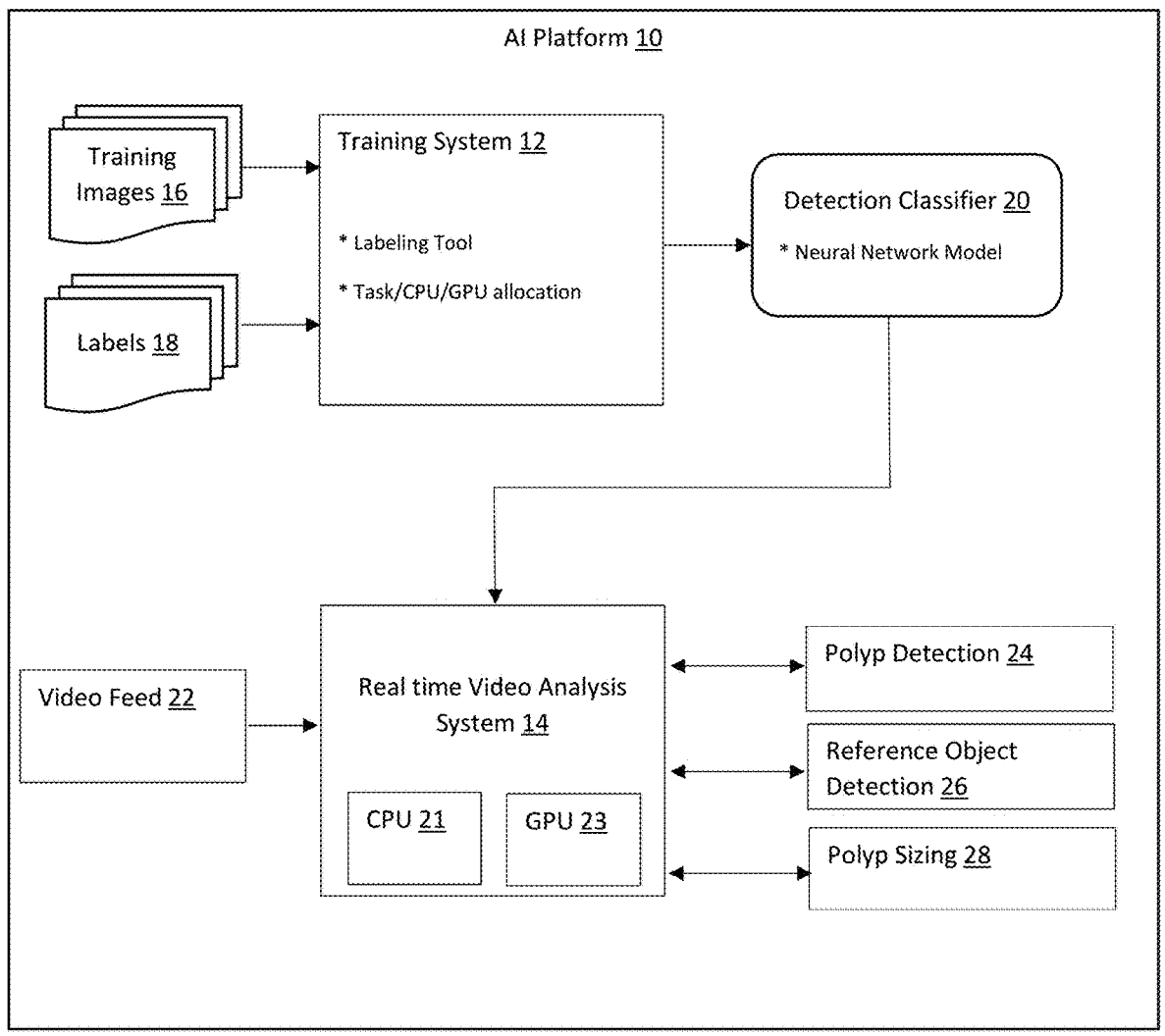
FIG. 1 shows an artificial intelligence platform according to embodiments.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Referring to FIG. 1, an artificial intelligence (AI) platform 10 is provided for detecting and sizing lesions during procedures in real-time. Note that while the embodiments are generally described with reference to detecting and sizing polyps, it is understood that the approach may be applied to any diseased tissue (i.e., lesions). AI platform 10 generally include: (1) a training system 12 that trains a detection classifier 20 based on a set of training images 16 and labels 18; and (2) a real time video analysis system 14 that utilizes the detection classifier 20 to analyze a video feed 22 in real-time to provide polyp detection 24 and polyp sizing 28. AI platform 10 may for example employ a neural network or other machine learning system.

In this illustrative embodiment, detection classifier 20 is trained with a deep learning system to detect both a lesion and a reference object, such as forceps, in the same image. (Alternatively, two detection classifiers 20 could be trained; one that detects lesions and one that detects reference objects.) As described herein, the reference object is utilized to facilitate sizing of the lesion.

Training images 16 may for example be obtained from frames in captured videos. Images used for training include random objects along with the desired objects, in this case polyps and have a variety of backgrounds and lighting conditions. Additionally, in some training images 16 the desired object is partially obscured, overlapped with something else, only halfway in the picture, etc.

Figure 2:
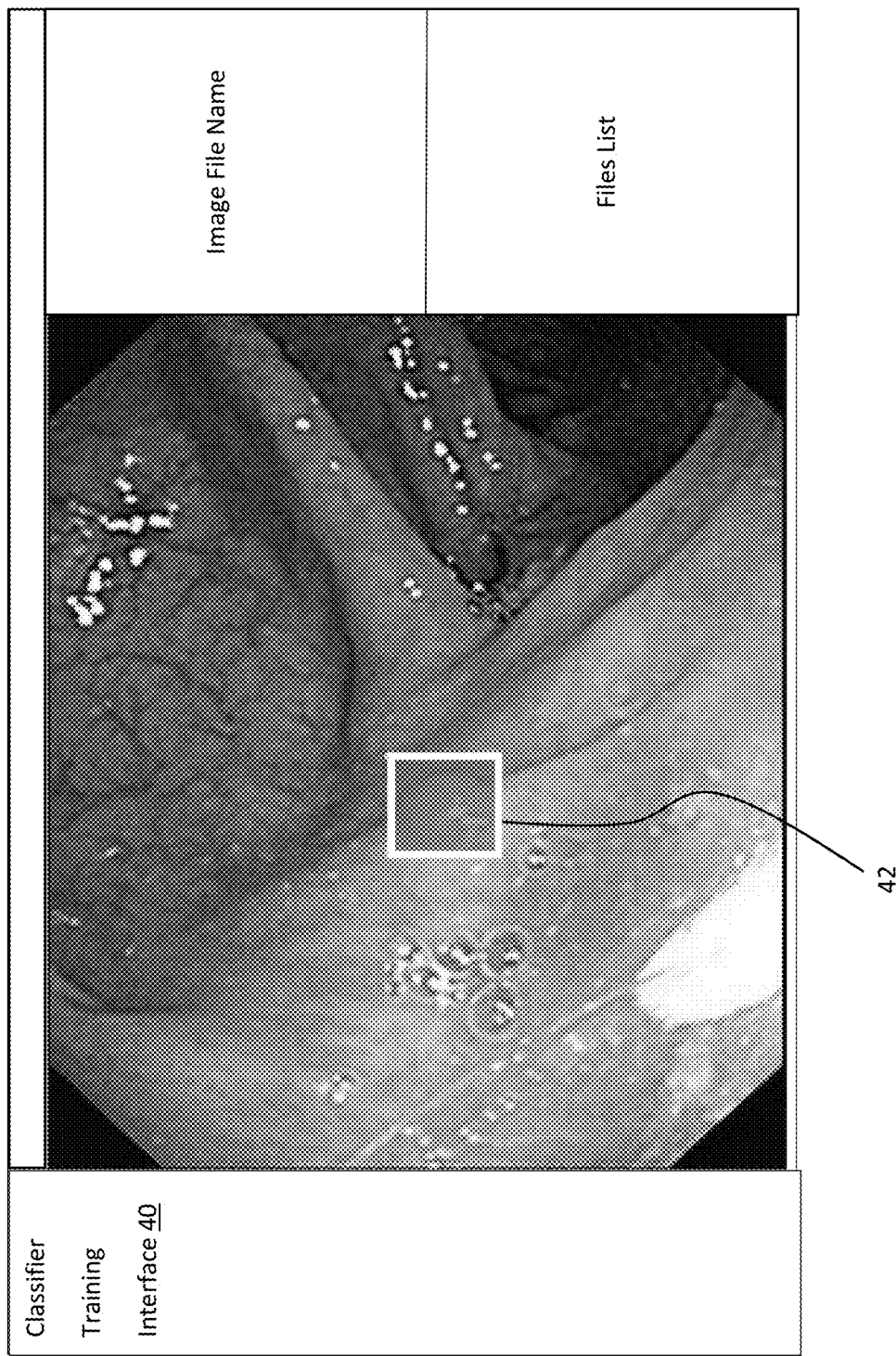
FIG. 2 shows an interface for training a classifier according to embodiments.
Figure 3:
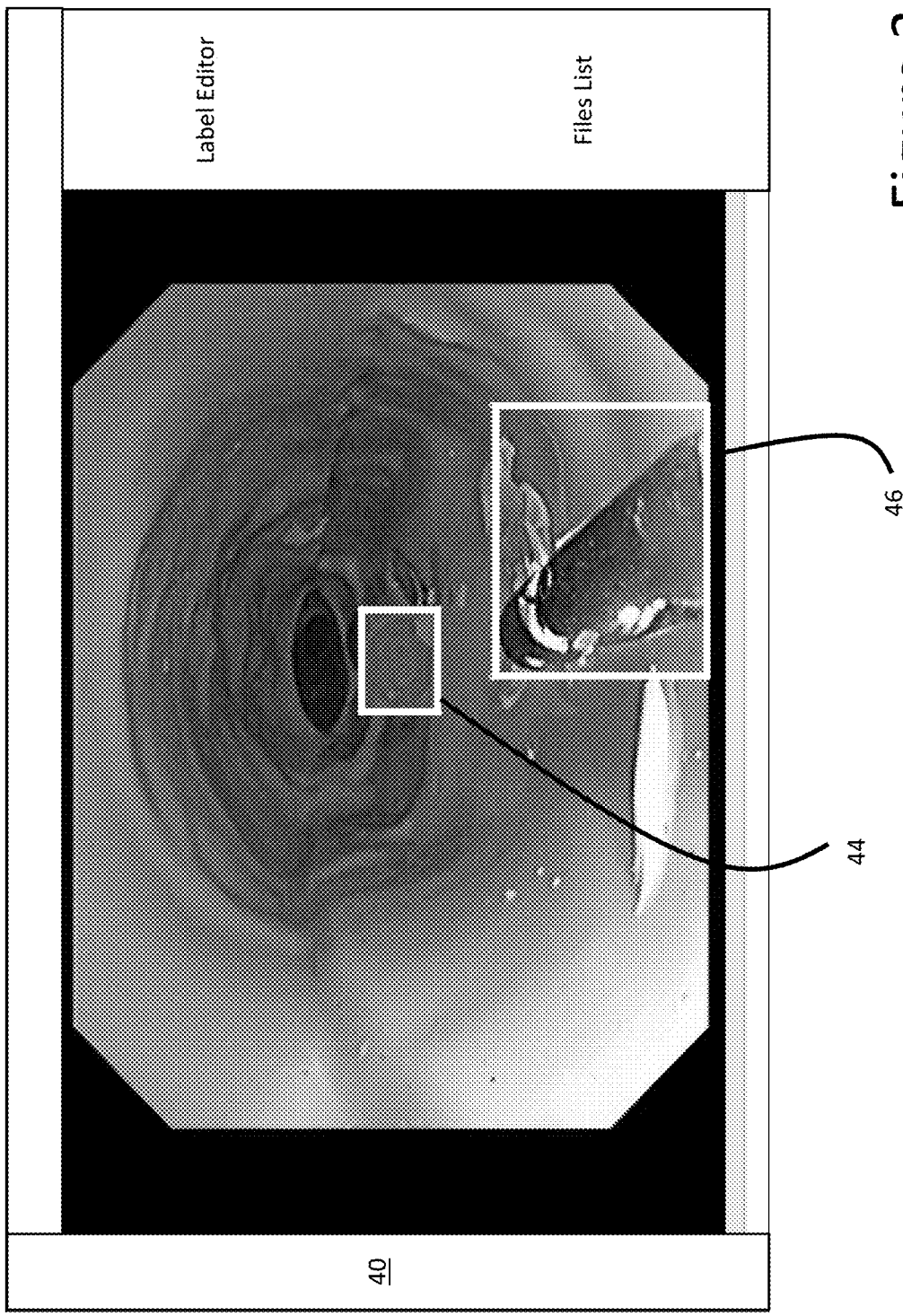
FIG. 3 shows a further interface for training a classifier according to embodiments.

Once a set of training images 16 have been gathered, they are tagged with labels 18 to reference the desired objects in every picture. The desired object can be a polyp or any other lesions, or some other object that could appear in a video feed 22, such as a finger, noise, shadows, etc. Any labeling system may be employed, such as LabelImg which is available as an open source on GitHub. FIG. 2 depicts an illustrative labeling tool 40 in which a user places a bounding box 42 around a lesion in a displayed training image 16 and selects a label for the type of lesion shown, e.g., a Pedunculated polyp, a Sessile polyp, a Flat polyp, etc. FIG. 3 depicts a further training image 16 in which a first bounding box 44 is placed around the lesion and a second bounding box 46 is placed around a reference object. In an illustrative embodiment, approximately 3000 training images 16 are used, in which each has a resolution of 1280×1024 pixels.

Once all of the training images 16 are labeled, training system 12 can be employed to train the detection classifier 20. Detection classifier 20 may for example comprise a neural network model into which the pixel data from each training image is processed. In one illustrative approach, an application programming interface (API) by TensorFlow™ can be used to construct the neural network model representative of a graph that includes nodes and edges. In this case, the model is mapped to underlying machine hardware. Nodes in the graph represent operations (e.g., machine learning functions, mathematical operations, etc.), and the edges represent the multidimensional data arrays also known as tensors communicated between the nodes. The unique edges, called control dependencies, can exist in the graph and denote that the source node must finish executing before the destination node starts executing. (TensorFlow provides a platform in which the designer's design algorithm flow and computation architecture is automatically optimized.) Nodes are assigned to computational devices and execute asynchronously, and in parallel once all the tensors on their incoming edges become available.

The video processing required in the AI platform 10 can be very expensive in terms of CPU power. Accordingly, certain computer-vision sub-tasks are allocated to special-purpose hardware architectures, such as a GPU 23 (graphics processing unit), while others are allocated to the CPU 21. The GPU 23, for example, is an accelerator that is available not only on desktop computers but also on mobile devices such as smartphones and tablets. Accordingly, the model used herein has the built-in ability to configure GPU usage along with CPU usage to utilize machine resources most efficiently.

The AI platform 10 may for example utilize a NVIDIA CUDA® Deep Neural Network library (cuDNN), which is a GPU-accelerated library of primitives for deep neural networks. cuDNN provides a highly tuned implementation of standard routines such as forward and backward convolution, pooling normalization, and activation layers. cuDNN provides high-performance GPU acceleration that automates low-level GPU performance tuning. AI platform 10 may also for example utilize a NVIDIA Quadro P5000 16GB-2560 CUDA CORES graphics card for development and testing. Anything above the NVIDIA GEFORCE GTX 1080-2560 CUDA CORES could likewise be utilized.

In the present case, the model is trained until the computed "loss" falls consistently below a threshold (e.g., 0.005 in the case of TensorFlow). Once training is completed, an inference graph representing the classification model is generated, which can then be deployed into the real-time video analysis system 14 (FIG. 1).

Once deployed, images from a video feed 22 (e.g., generated during a procedure) can be analyzed by the real-time video analysis system 14 to provide polyp detection 24 and reference object detection 26 (to determine polyp sizing 28). FIG. 4 depicts an illustrative .xml file for an image in the video feed 22 that includes an identified forceps and polyp.

In this two-step process, a lesion is first detected in real time while the clinician is doing the procedure. Next, the size of the lesion is calculated using the reference object, and then an indication of the lesion and size are output with a video feed. In a typical procedure involving polyps, forceps are used during a clinical procedure for intervention. Forceps comprise a slender flexible tool with movable cup-shaped jaws used to obtain biopsy specimens. Actual polyp size is determined based (1) on the measurement of the polyp size in pixels, (2) measurement of the size of the forceps in pixels, and (3) recalculation of the actual polyp size into a unit of length (e.g., millimeters) based on the known size of the forceps.

Figure 5:
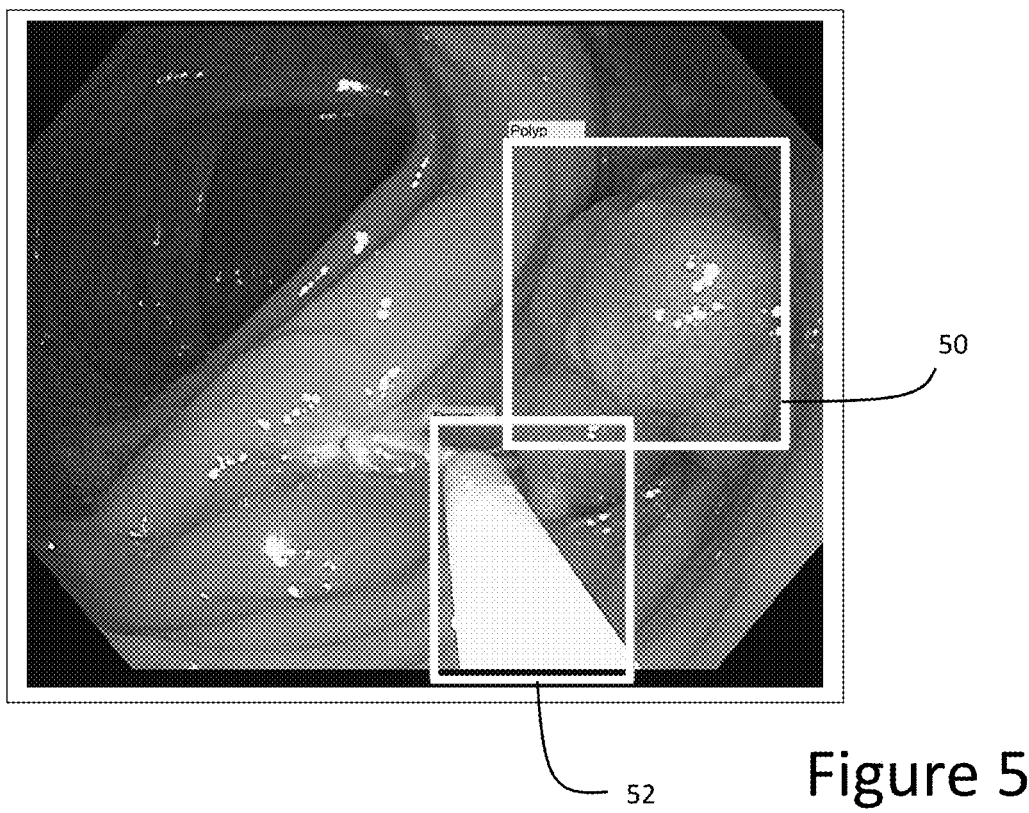
FIG. 5 depicts a process for capturing image data of polyp and forceps according to embodiments.
Figure 6:
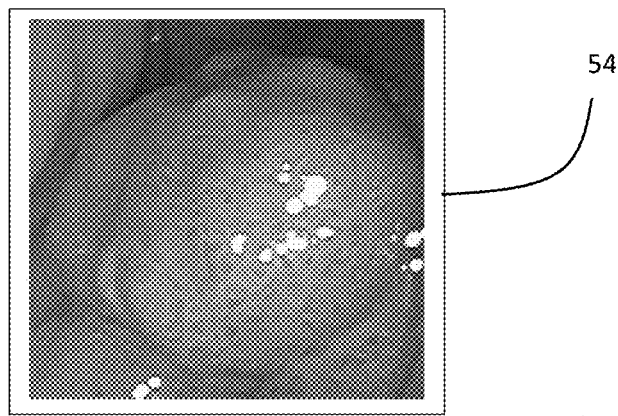
FIG. 6 depicts a cut out rectangle of a polyp image from FIG. 5 according to embodiments.

As shown in FIG. 5, when the system identifies a polyp and the forceps in the same video frame, circumscribed rectangles around a polyp 50 and forceps 52 are defined and the coordinates of the corners of the rectangles get recorded. The area defined by the circumscribed rectangle around the polyp 50 gets cut out of the frame into a separate image 54 shown in FIG. 6. A similar separate cut out image is created for the reference object (not shown).

Figure 7:
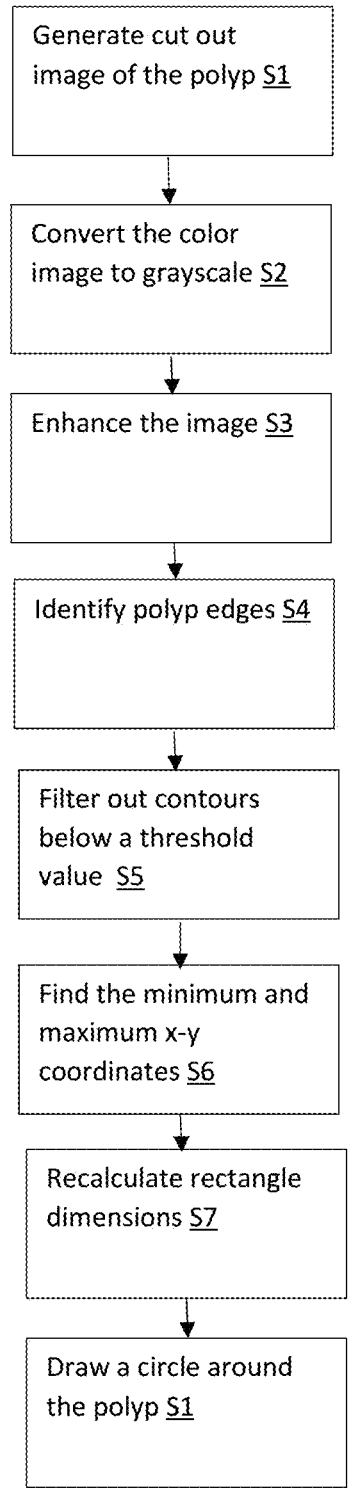
FIG. 7 depicts a flow diagram of a process of calculating a pixel size of a polyp according to embodiments.
Figure 8:
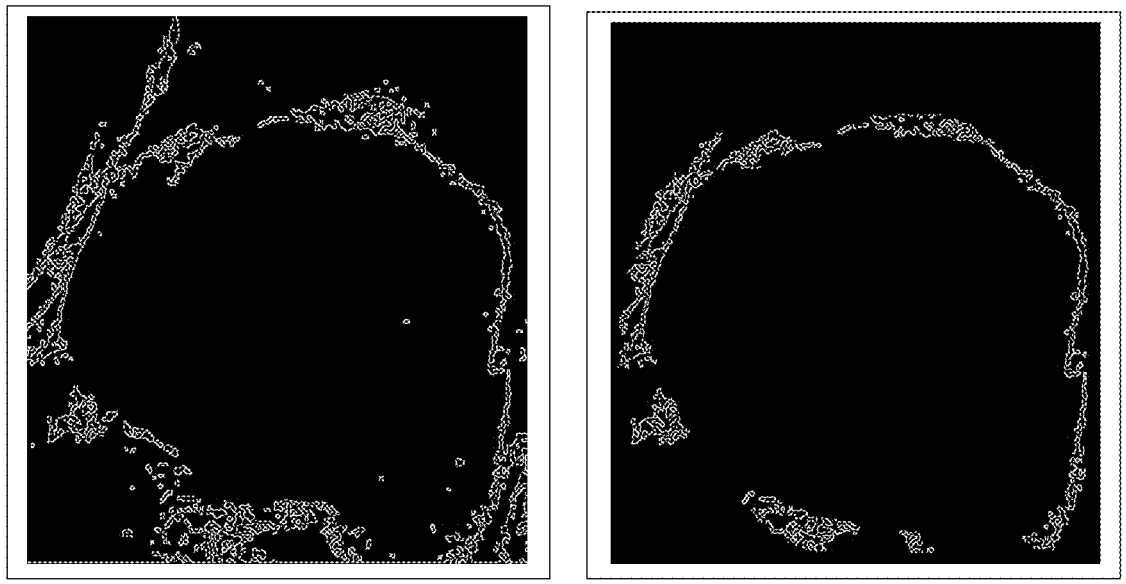
FIG. 8 depicts a pair contour images of a polyp according to embodiments.

FIG. 7 describes an illustrative method for processing the polyp image data. First, at S1, a rectangular cut out image 54 (FIG. 6) containing the polyp is obtained (e.g., as an RGB image). Next, at S2, the RGB image gets split into three monochrome channels: Red, Green, and Blue and is converted into a grayscale image. At S3, the image gets smoothed by applying a Gaussian function to reduce image details and variation of brightness thus enhancing image structure. At S4, the polyp edges or contours are identified, e.g., using a Canny multi-stage edge detection algorithm, and at S5, multiple polyp contours are identified using an OpenCV function. The contours that fall below a threshold, e.g., contain less than 50 pixels, get filtered out. An example of this process is shown in FIG. 8 in which the image on right depicts a filtered contour image and the image on the left depicts an unfiltered contour image.

At S6, for all remaining contours, the minimum and maximum x and y-coordinates are determined (i.e., Xmin; Xmax; Ymin; Ymax). At S7, rectangle dimensions 50 for the polyp are recalculated. The new coordinates are defined as:

$$X\text{new}=X+X\min; Y\text{new}=Y+Y\min.$$

The rectangle dimensions are recalculated as:

$$\text{Height } H=Y\max-Y\min;$$

$$\text{Width } W=X\max-X\min.$$

The larger of the two dimensions equals the polyp size in pixels (Dpx), e.g., 220×280 pixels. At S8, a circle is drawn around the polyp. The coordinates of the center of the circle denoted as:

$$Xc=X\text{new}+W/2; Yc=Y\text{new}+H/2;$$

In which the diameter of the circle Dc=Dpx.

Figure 9:
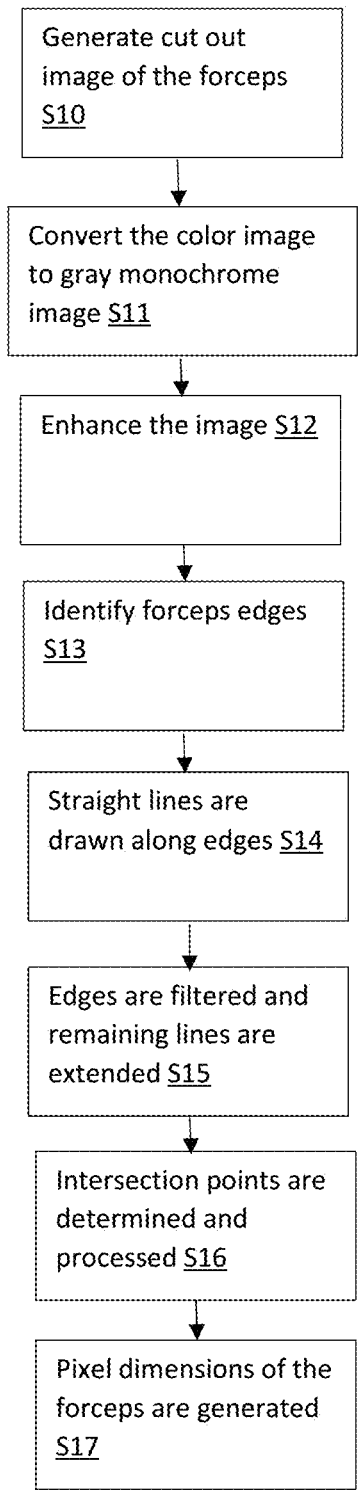
FIG. 9 depicts a flow diagram of a process of calculating a pixel size of a forceps according to embodiments.
Figure 10:
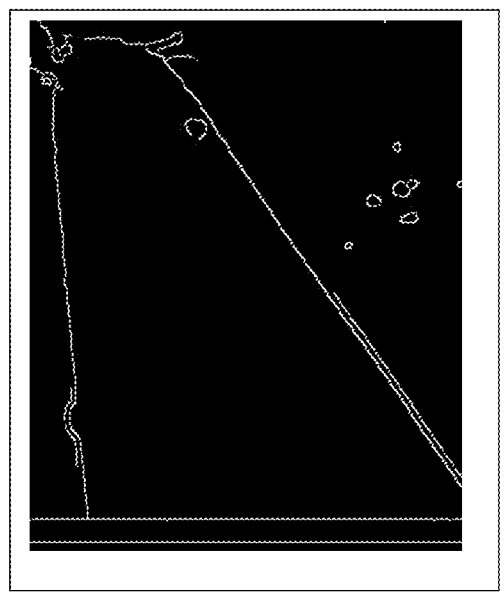
FIGS. 10-13 depict line image data used to calculate a pixel size of a forceps according to embodiments.

FIG. 9 depicts an illustrative process for calculating the pixel size of the forceps. At S10, the area defined by a circumscribed rectangle around the forceps gets cut out of the frame into a separate image, and at S11, the color image is converted into a gray monochrome image. At S12, the image gets smoothed by applying, e.g., a Gaussian function to reduce image details and variation of brightness thus enhancing image structure, and at S13, the forceps edges are identified using, e.g., Canny multi-stage edge detection algorithm. At S14, straight lines are drawn along the forceps edges using a Hough transform technique, e.g., illustrative result shown in FIG. 10.

At S15, edges are filtered and processed as follows. The number of lines gets reduced by filtering out short lines (e.g., less than 10 pixels). A straight line may be represented by equation:

$$y=mx+b.$$

For the remaining lines, the coefficients m and b and their angles of inclination to the x-axis are calculated. The lines with angles of inclination, e.g., less than 21° and greater than 150° are removed. The lines remaining on the image get extended to the image boundaries. The coordinates of intersection points (midpoints) of the lines with the horizontal boundaries of the image are calculated.

The groups of lines having a difference between their coefficients m<0.307 or angles of inclination <2° and a difference between x coordinates of their intersection points with the upper horizontal boundary of the image <20 pixels get replaced with a fewer number of midlines. A coefficient m of a midline for each group is calculated as follows:

$$m=(m1+m2+\ldots+mn)/n;$$

A coefficient b for a midline is calculated as follows:

$$b=(b1+b2+\ldots+bn)/n$$

With several lines remaining on the image, the ones having an x-coordinate of the intersection points with the lower horizontal boundary of the image at a distance of 30 pixels or more from the left or right vertical image boundaries get removed.

Figure 11:
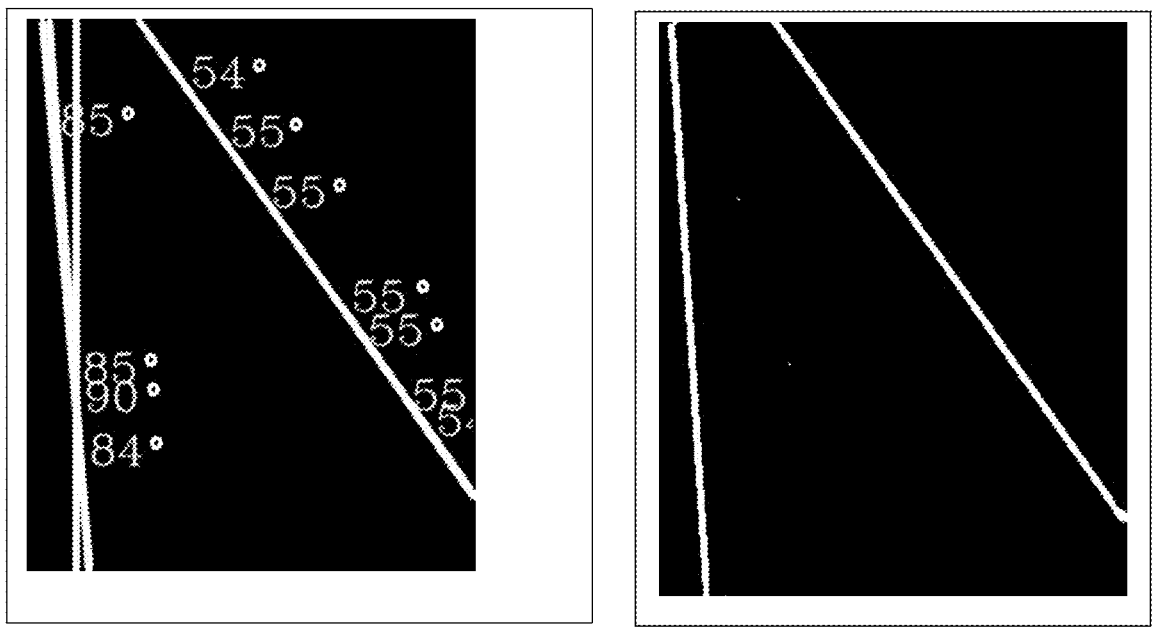

Further line filtering leaves only two lines on the image: "left line", having a minimum x-coordinate ("x-left") of the intersection point with the upper horizontal image boundary and "right line" having a maximum x-coordinate ("x-right") of the intersection point with the upper horizontal image boundary, as shown in FIG. 11. If the intersection point of the left line and the right line is located inside the image boundaries, the frame is considered not fit for the forceps size calculations. Another frame with a different forceps location must be taken. If the intersection point of the left line and the right line is located outside of the image boundaries, then the angles of inclination of the lines to the x-axis are evaluated.

Figure 12:
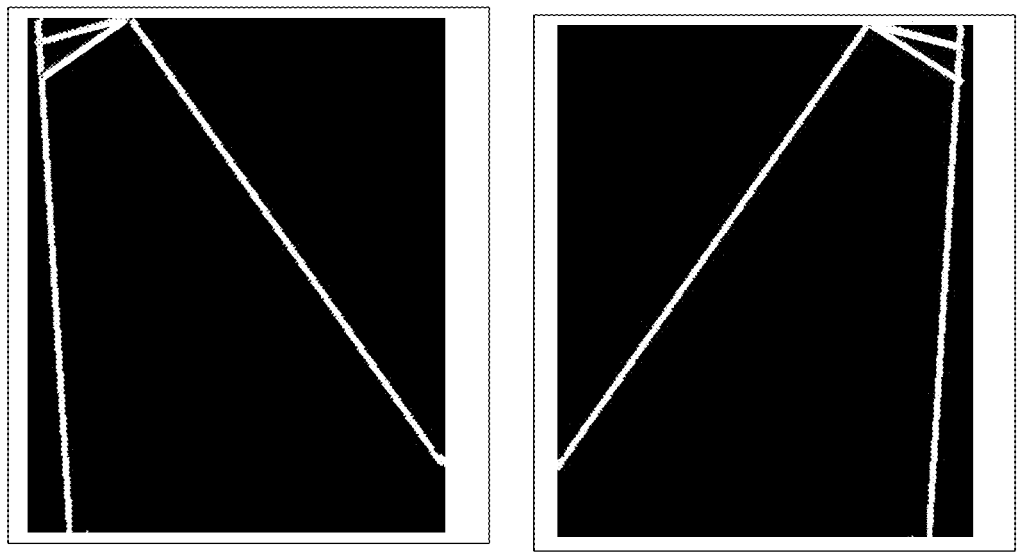

As shown in FIG. 12, if an angle of inclination of both lines less than or equal to 90° then a perpendicular to the right line is drawn from the intersection point of the right line with the upper image boundary towards the left line until the perpendicular crosses the left line (left image). If an angle of inclination of both lines is greater than or equal to 90° then a perpendicular to the left line is drawn from the intersection point of the left line with the upper image boundary towards the right line until the perpendicular crosses the right line (right image). A size of the forceps in pixels (Fpx) is the mean of the length of the perpendicular between the left and right lines and a distance between x-left and x-right points.

Figure 13:
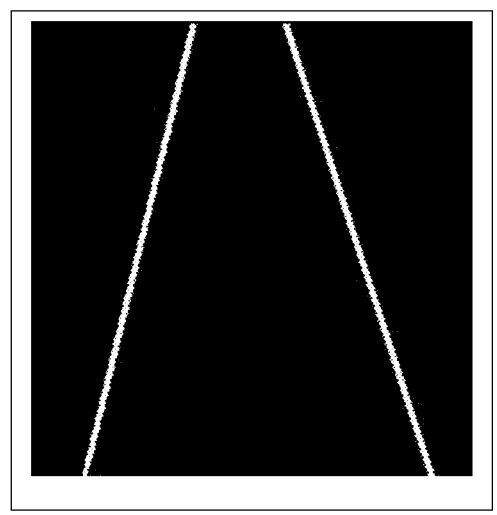

If an angle of inclination of the left line >90° and an angle of inclination of the right line <90°, then a size of the forceps in pixels (Fpx) is considered equal to the distance between x-left and x-right points (FIG. 13).

Once the pixel sizes of the both the polyp and forceps are calculated as above, the actual size of the polyp, e.g., in millimeters (mm) is determined as follows. A size of the forceps in mm (Fmm) is available, e.g, based on the device model or actual measurement. A polyp size in mm (Dmm) is then calculated as follows and may be rounded to the whole mm:

$$D\text{mm}=(D\text{px}*F\text{mm})/F\text{px}$$

Once a poly is detected during a medical procedure, a polyp size in mm is outputted, e.g., on a computer screen in real time with the video feed.

As described, the AI platform 10 is utilized for detecting and sizing lesions. Additionally, the described platform 10 can also be very useful in early detection other diseases as well. The classifier can be trained to detect diseases such as Inflammatory Bowel Disease (IBD). Inflammatory bowel disease is an umbrella term used to describe disorders that involve chronic inflammation of your digestive tract. Types of IBD include ulcerative colitis, which causes long-lasting inflammation and sores (ulcers) in the innermost lining of the large intestine (colon) and rectum. Another type of IBD is Crohn's disease, which is characterized by inflammation of the lining of the digestive tract, which often spreads deep into affected tissues. IBD can be debilitating and sometimes leads to life-threatening complications, and increases the risk of colon cancer.

The AI platform 10 can further be used in comparing the size (area) before and after the treatment of the inflammation of the lining of the digestive tract which may appear in patches in Crohn's disease or a continuous pattern in Ulcerative colitis as well as early detection of precancerous lesions in patients with Crohn's and Ulcerative colitis.

Additionally, a machine-learned model to automatically detect the location of the diseases is another way in which this AI platform 10 can be useful. Accurate detection of the location of the disorders can be beneficial for the surgeons who perform a surgical treatment of the diseases after once a clinical procedure has been performed.

Further, determining Gastroenterology (GI) quality metrics is another AI platform 10 application. This would allow automated measurement of several metrics that likely reflect the quality of a GI clinical procedure.

Further, the process can be used to analyze digitized image frames captured during colonoscopy procedure. Information like insertion time, withdrawal time, images at the time of maximal intubation, Cecal intubation time, and landmark identified, quality of bowel prep can be automatically measured with the described method. As these metrics can be obtained automatically, it will help to quantify health-care processes and can aid in providing high-quality health care.

The primary colonoscopy quality indicator is the adenoma detection rate (ADR), which is defined as the proportion of an endoscopist's screening colonoscopies in which one or more adenomas have been detected. To maximize adenoma detection, adequate mucosal inspection is required to ensure complete examination. Studies of tandem colonoscopies have revealed that physicians may miss adenomas larger than 1 cm. to ensure adequate adenoma detection, studies have suggested that a physician's withdrawal time, not including polyp resection, should be on average at least 6-9 min. A paper published in 2006 by the ASGE/ACG Taskforce on Quality in Endoscopy recommended that the withdrawal time should be measured as an aggregate of a physician's practice rather than based on an individual patient given the variation in anatomy such the prominence of colonic folds.

Another quality measure that affects adenoma detection is the quality of the bowel preparation. An adequate colon preparation is vital to ensure complete mucosal inspection. It has been reported that only three quarter of colonoscopies have an adequate colon preparation. High rates of missed adenomas and advanced neoplasia have been observed in patients with suboptimal colon preparations.

How should a physician ensure a quality colonoscopy for CRC screening in their practice? Despite some limitations, the ADR should be calculated for each endoscopist based on data from screening examinations. If a physician's ADR is lower than the benchmark of 20%, quality improvement efforts are needed to increase this rate. Physicians should aim to achieve cecal intubation rates of 95% or greater in screening colonoscopies. Techniques for mucosal examination with a focus on mean withdrawal time should be assessed. The quality of bowel preparation in the endoscopy practice should also be determined and optimized. Finally, in adequately prepped and carefully examined colons, compliance with screening and surveillance guidelines for future exams is strongly recommended. These steps will ensure that colonoscopy is maximally effective in preventing CRC.

Figure 14:
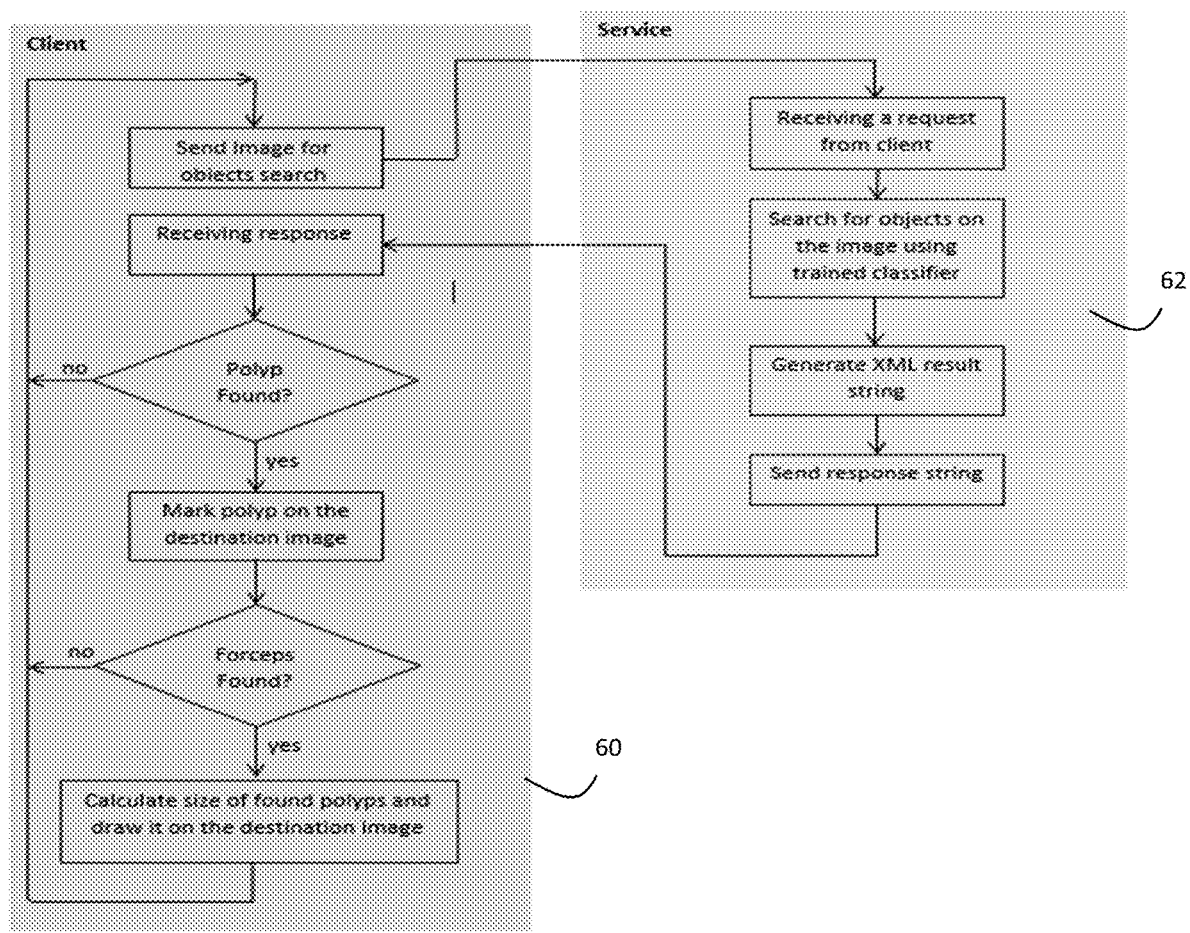
FIG. 14 depicts a client-service flow diagram of a process according to embodiments.

FIG. 14 depicts an overview of an illustrative process of implementing a client-service model using the real time video analysis system 14 of FIG. 1. On the client 60 10 (e.g., where the procedure is being performed), a video frame (image) is captured and is forwarded to a service 62 (e.g., a remote server). The service 62 receives the request, and searches for objects using a trained classifier. An XML result string is generated and is sent back to the client 60 in real time.

The client 60 receives the response and analyzes the XML string to determine if a polyp was found. If no, a next image is sent to the service 62. If yes, the polyp is indicated as detected with the video feed (i.e., on a computer screen). Next a determination is made whether forceps were also found in the image. If no, a next image is sent to the service 62. If yes, the size of the polyp is calculated and output with the video feed.

In a further embodiment, the AI platform may be employed in Video Capsule Endoscopy (VCE), which is a procedure that uses a tiny wireless camera to take pictures of the digestive tract. A capsule endoscopy camera sits inside a capsule which a patient swallows. As the capsule travels through the digestive tract, the camera takes thousands of pictures that get transmitted to a recorder that the patient wears, e.g., on a belt around their waist.

VCE helps doctors see inside the small intestine, an area that is hard to reach with more traditional endoscopy procedures. Traditional endoscopy involves passing a long, flexible tube equipped with a video camera down the throat or through the rectum.

The camera used in capsule endoscopy takes thousands of color photos as it passes through the digestive tract. The images saved on the recorder then gets transferred to a computer with special software that strings the images together to create a video.

Once the video gets created, the doctor watches the video to look for abnormalities within the digestive tract. The processes of watching the entire VCE of the small intestine takes about 45 minutes to 1 hour. In addition to using it in real time clinical procedure, the artificial intelligence (AI) platform can also be used to analyze these videos in order to detect lesions, which can then be evaluated by a clinician.

A method for detecting the lesion in a saved video, e.g., from a VCE procedure, using artificial intelligence (AI) may for example include the steps of: providing a trained classifier that includes a deep learning model trained to detect lesions; processing a video after it has been created using the transferred images from the recorder; and using the trained classifier to determine if a video frame from the video has a lesion.

It is understood that AI platform 10, client 60, and service 62 described herein may be implemented as a computer program product stored on a computer readable storage medium. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Python, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A computing system may comprise any type of computing device and for example includes at least one processor, memory, an input/output (I/O) (e.g., one or more I/O interfaces and/or devices), and a communications pathway. In general, processor(s) execute program code which is at least partially fixed in memory. While executing program code, processor(s) can process data, which can result in reading and/or writing transformed data from/to memory and/or I/O for further processing. The pathway provides a communications link between each of the components in computing system. I/O can comprise one or more human I/O devices, which enable a user to interact with computing system. Computing system may also be implemented in a distributed manner such that different components reside in different physical locations.

Furthermore, it is understood that the AI platform 10 or relevant components thereof (such as an API component, agents, etc.) may also be automatically or semi-automatically deployed into a computer system by sending the components to a central server or a group of central servers. The components are then downloaded into a target computer that will execute the components. The components are then either detached to a directory or loaded into a directory that executes a program that detaches the components into a directory. Another alternative is to send the components directly to a directory on a client computer hard drive. When there are proxy servers, the process will select the proxy server code, determine on which computers to place the proxy servers' code, transmit the proxy server code, then install the proxy server code on the proxy computer. The components will be transmitted to the proxy server and then it will be stored on the proxy server.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An artificial intelligence (AI) platform for detecting and sizing a lesion in real time during a clinical procedure, comprising:
    a trained classifier that includes a deep learning model trained to detect lesions and reference objects in image data; and
    a real time video analysis system that receives a video feed during a clinical procedure, uses the trained classifier to determine if a video frame from the video feed has both a lesion and a reference object, calculates an actual size of the lesion based on a pixel size of both the lesion and the reference object, and outputs an indication that the lesion was detected and the actual size of the lesion;
    wherein the pixel size of the lesion is determined by:
        capturing a rectangular cut out image containing the lesion;
        enhancing the cut out image using Gaussian smoothing;
        using an edge detection algorithm to detect contours of the lesion; and
        calculating new rectangular coordinates of the lesion to provide a pixel size of the lesion (Dpx).

2. The AI platform of claim 1, wherein the lesion comprises a polyp.

3. The AI platform of claim 1, wherein the reference object includes at least one of a snare or a forceps.

4. The AI platform of claim 1, wherein the trained classifier includes a neural network that was trained with a set of training images, in which a subset of the training images includes polyps of different types, polyps appearing on different background, and polyps appearing in different lighting conditions.

5. The AI platform of claim 1, wherein the indication that the lesion was detected and the actual size of the lesion is outputted the video feed during the clinical procedure.

6. The AI platform of claim 1, wherein the pixel size of the reference object is determined by:
    capturing a rectangular cut out image containing the reference object and converting the cut out image to a gray monochrome image;
    enhancing the cut out image using Gaussian smoothing;
    identifying edges of the reference object and imposing straight lines along the edges;
    filtering the straight lines to identify a pair of intersecting lines; and
    determining a pixel size of the reference object (Fpx) based on the pair of intersecting lines.

7. The AI platform of claim 6, wherein the actual size of the lesion D is calculated as:

$$D=(Dpx*F)/Fpx,$$

wherein F is an actual size of the reference object.

8. A method for detecting and sizing a lesion in real time during a clinical procedure using artificial intelligence (AI), comprising:
    providing a trained classifier that includes a deep learning model trained to detect lesions and reference objects in image data;
    processing a video feed during a clinical procedure;
    using the trained classifier to determine if a video frame from the video feed has both a lesion and a reference object;
    calculating an actual size of the lesion based on a pixel size of both the lesion and the reference object, wherein the pixel size of the lesion is determined by:
        capturing a rectangular cut out image containing the lesion;
        enhancing the cut out image;
        using an edge detection algorithm to detect contours of the lesion; and
        calculating new rectangular coordinates of the lesion based on the contours to provide a pixel size of the lesion (Dpx); and
    outputting an indication that the lesion was detected and the actual size of the lesion.

9. The method of claim 8, wherein the lesion comprises a polyp.

10. The method of claim 8, wherein the reference object comprises a snare.

11. The method of claim 8, wherein the reference object comprises forceps.

12. The method of claim 8, wherein the trained classifier includes a neural network that was trained with a set of training images, in which a subset of the training images includes polyps of different types, polyps appearing on different backgrounds, and polyps appearing in different lighting conditions.

13. The method of claim 8, wherein the indication that the lesion was detected and the actual size of the lesion is outputted with the video feed during the clinical procedure.

14. The method of claim 8, wherein the pixel size of the reference object is determined by:
    capturing a rectangular cut out image containing the reference object;
    enhancing the cut out image using Gaussian smoothing;
    identifying edges of the reference object and imposing straight lines along the edges;
    filtering the straight lines to identify a resulting pair of intersecting lines; and
    determining a pixel size of the reference object (Fpx) based on the resulting pair of intersecting lines.

15. The method of claim 14, wherein the actual size of the lesion D is calculated as:

$$D=(Dpx*F)/Fpx,$$

wherein F is an actual size of the reference object.

16. A computer program product stored on a computer readable storage medium, which when executed by a computing system, detects and sizes a lesion in real time during a clinical procedure using artificial intelligence (AI), the program product comprising:
  program code that processes a video feed during a clinical procedure;
  program code that uses a trained classifier to determine if a video frame from the video feed has both a lesion and a reference object;
  program code that calculates an actual size of the lesion based on a pixel size of both the lesion and the reference object, wherein the reference object includes a tool configured to biopsy the lesion and the pixel size of the reference object is determined by:
    placing a bounding box around the reference object;
    imposing lines along detected edges of the reference object; and
    calculating the pixel size of the reference object based on a distance between two lines; and
  program code that outputs an indication that the lesion was detected and the actual size of the lesion.

17. The program product of claim 16, wherein the lesion comprises a polyp and the reference object comprises forceps.

18. The program product of claim 16, wherein the indication that the lesion was detected and the actual size of the lesion is outputted with the video feed during the clinical procedure.

19. An artificial intelligence (AI) platform for detecting and sizing a lesion in real time during a clinical procedure, comprising:
  a trained classifier that includes a deep learning model trained to detect lesions and reference objects in image data; and
  a real time video analysis system that receives a video feed during a clinical procedure, uses the trained classifier to determine if a video frame from the video feed has both a lesion and a reference object, calculates an actual size of the lesion based on a pixel size of both the lesion and the reference object, and outputs the actual size of the lesion, wherein the reference object includes a tool used in the procedure configured to biopsy the lesion and wherein the pixel size of the reference object is determined by evaluating inclination angles of a pair of detected edges of the reference object.

* * * * *